United States Patent [19]

Jackson et al.

[11] Patent Number: 5,776,709

[45] Date of Patent: *Jul. 7, 1998

[54] METHOD FOR PREPARATION AND ANALYSIS OF LEUKOCYTES IN WHOLE BLOOD

[75] Inventors: Anne Louise Jackson, Ridgefield, Wash.; Robert Alan Hoffman, Livermore, Calif.; Andrew D. Blidy, Redwood City, Calif.; Kenneth Earl Murchison, Ben Lomond, Calif.; Pierre Bierre, Redwood City, Calif.; Dan E. Thiel, Pleasanton, Calif.

[73] Assignee: Becton Dickinson and Company, Franklin Lakes, N.J.

[ * ] Notice: The term of this patent shall not extend beyond the expiration date of Pat. No. 5,627,040.

[21] Appl. No.: 286,094

[22] Filed: Aug. 4, 1994

Related U.S. Application Data

[63] Continuation of Ser. No. 15,759, Feb. 10, 1993, abandoned, Continuation-in-part of Ser. No. 846,316, Mar. 5, 1992, abandoned, which is a continuation-in-part of Ser. No. 751,020, Aug. 28, 1991, abandoned.

[51] Int. Cl.[6] .................................................. G01N 33/533
[52] U.S. Cl. .................... 435/7.24; 435/808; 436/526; 436/171; 436/800; 436/805; 356/336; 356/338
[58] Field of Search .................... 435/7.24, 808; 436/526, 172, 800, 805; 364/413.01, 413.08, 413.13; 386/14, 16, 22, 25, 36, 38, 48

[56] References Cited

U.S. PATENT DOCUMENTS

| | | |
|---|---|---|
| 4,284,412 | 8/1981 | Hansen et al. . |
| 4,654,312 | 3/1987 | Chang et al. ........................ 436/519 |
| 4,727,020 | 2/1988 | Recktenwald ........................ 435/6 |
| 4,751,179 | 6/1988 | Ledis ........................ 435/34 |
| 4,805,225 | 2/1989 | Clark ........................ 382/15 |
| 4,902,613 | 2/1990 | Chang et al. ........................ 435/2 |
| 4,965,725 | 10/1990 | Rutenberg ........................ 364/413.1 |
| 4,987,086 | 1/1991 | Brosnan et al. ........................ 436/501 |
| 5,017,497 | 5/1991 | de Grooth et al. ........................ 436/63 |
| 5,030,554 | 7/1991 | Quintana et al. ........................ 435/2 |
| 5,041,733 | 8/1991 | Noguchi et al. ........................ 250/461.2 |
| 5,047,321 | 9/1991 | Loken et al. ........................ 435/6 |
| 5,138,170 | 8/1992 | Noguchi et al. ........................ 250/461.2 |
| 5,144,224 | 9/1992 | Larsen ........................ 324/71.4 |

FOREIGN PATENT DOCUMENTS

| | | |
|---|---|---|
| 0 314 406 | 5/1989 | European Pat. Off. . |
| WO 88/07187 | 9/1988 | WIPO . |
| WO 9305478 | 3/1993 | WIPO . |

OTHER PUBLICATIONS

Horan, et al. "Improved flow cytometric analysis of leukocyte subsets: Simultaneous identification of five cell subsets using two–color immunofluorescence" *PNAS* 83:8361–8365 (1986).

Begg, et al. "Cell Kinetic Analysis of Mixed Populations Using Three–Color Fluorescence Flow Cytometry" *Cytometry* 12:445–454 (1991).

R. P. Lippmann "An Introduction to Computing with Neural Nets" *IEEE ASSP Magazine* pp. 4–22, Apr. 1987.

F. F. Mandy, et al. "Automated Software for Rapid Analysis of List Mode Data From Simultaneous Three Color Flow Cytometry" *Cytometry* Suppl. 5:135 (1991) Abstract 741C.

(List continued on next page.)

*Primary Examiner*—Carol A. Spiegel
*Attorney, Agent, or Firm*—Susan A. Capello; Royal N. Ronning, Jr.

[57] ABSTRACT

A method of flow cytometric analysis of leukocyte subpopulations using a fluorescence trigger and gating on light scatter vs. fluorescence. The methods are useful where light scatter parameters are unsatisfactory for identification of leukocyte subpopulations, for example when analyzing lysed blood samples without removal of lysing reagent or unbound label prior to analysis.

2 Claims, 10 Drawing Sheets

OTHER PUBLICATIONS

F. F. Mandy, et al. "Cell Lineage Specific Gating Method for T Cell Subset Analysis" *Cytometry* Suppl. 5:79 (1991) Abstract 399C.

K. Shults, et al. "CD45 Antigen Density Versus RALS: New Tool for Analysis for Blood and Bone Marrow" *Cytometry* Suppl. 5:79 (1991) Abstract 400D.

C. W. Caldwell, et al. "A Rapid, No-Wash Technic for Immunophenotypic Analysis by Flow Cytometry" *Am. J. Clin. Pathol.* 86:600–607 (1986).

R. A. Hoffman "Immunofluorescence Analysis of Leukocytes Without Red Cells Lysis" *Cytometry* Suppl. 1:36 (1987) Abstract 172.

L.W.M.M. Terstappen, et al. "A Rapid Sample Preparation Technique for Flow Cytometric Analsysis of Immunofluorescence Allowing Absolute Enumeration of Cell Populations" *J. Immunol. Mtds.* 123:103–112 (1989).

M.R. Loken, et al. "Establishing Optimal Lymphocyte Gates for Immunophenotyping by Flow Cytometry" *Cytometry* 11:453–459 (1990).

Ortho Diagnostic Systems, Inc. "Direct Immunofluorescence Prodedure for Whole Blood Analysis of Leukocyte Subsets by Flow Cytometry" Published as a Laboratory Method by ODSI, Jan. 1985.

D. D. Egbert, et al. "Preprocessing of Biomedical Images for Neurocomputer Analysis" *IEEE Int. Conf. on Neural Networks* IEEE, pub., New York, N.Y. pp. 561–568 (1988).

Y. Imasato, et al. "CYBEST—Automated Pap Smear Prescreener" *Toshiba Review* (*Intl. Ed.*) n 100, pp. 60–63, Nov.–Dec. 1975.

METHOD FOR PREPARATION AND ANALYSIS OF LEUKOCYTES IN WHOLE BLOOD

This application is a continuation of application U.S. Ser. No. 08/015,759, filed Feb. 10, 1993 and now abandoned, which is a continuation-in-part of application U.S. Ser. No. 07/846,316, filed Mar. 5, 1992 and now abandoned, which is a continuation-in-part of PCT application No. US 92/072921, filed Aug. 28, 1992 and now published as WO 93/05478, which is a continuation-in-part of application U.S. Ser. No. 07/751,020, filed Aug. 28, 1991 and now abandoned.

FIELD OF THE INVENTION

The present invention relates to a method for distinguishing and identifying leukocyte subpopulations in a blood or bone marrow sample. More particularly, the invention relates to methods for distinguishing and identifying subpopulations of leukocytes in a blood or bone marrow sample by flow cytometry using fluorescence and light scattering characteristics of the leukocytes.

BACKGROUND OF THE INVENTION

In the field of hematology it is often useful to distinguish and identify the various types of white blood cells (leukocytes) which are present in the blood or bone marrow. Analysis of subpopulations of leukocytes is of particular interest for evaluation of immune system-related diseases such as acquired immune deficiency syndrome (AIDS). In particular, analysis of lymphocytes, a mononuclear leukocyte involved in the immune response, has clinical significance for management of immune system disorders. For example, it may be useful to detect or quantify the proportions of T-cell and B-cell subsets, the helper/inducer subsets of T-cells or the suppressor/cytotoxic subsets of T-cells. Monocytes, granulocytes (neutrophils), eosinophils and basophils are other leukocyte subpopulations of clinical interest in addition to lymphocytes. These cell types can be resolved and analyzed by flow cytometry.

Flow cytometers are useful for detecting particles such as cells. These instruments have means for detecting forward scattered and side scattered light as well as one or more means for detecting fluorescence. Forward and side light scatter are used to determine physical parameters, e.g. cell size and granularity. The various fluorescence detectors are used to distinguish cells labeled with fluorochromes which can be excited to emit light at different wavelengths. Examples of fluorochromes known in the art for use in flow cytometry are fluorescein isothiocyanate (FITC), phycoerythrin (PE), propidium iodide (PI) and peridinin chlorophyll protein (PerCP). All of these fluorochromes can be excited using light having a wavelength of 488 nm, but their emission wavelengths are different. FITC emits fluorescence at about 530 nm, PE and PI emit fluorescence at about 570 nm and PerCP emits fluorescence at about 670 nm, thereby permitting detection of three fluorescences of different colors using a single excitation wavelength.

To analyze a particular subpopulation of leukocytes by flow cytometry, the flow cytometer is set to trigger on a selected parameter. "Trigger" refers to a preset threshold for detection of a parameter. It is typically used as a means for detecting passage of a cell or other particle through the laser beam. Detection of an event which exceeds the threshold for the selected parameter triggers acquisition of light scatter and fluorescence data for the particle. Data is not acquired for cells or particles which cause a response below the threshold. The trigger parameter is typically the detection of forward scattered light caused by passage of a cell or particle through the light beam. The flow cytometer then detects and collects the light scatter and fluorescence data for the cell.

A particular subpopulation of interest is then further analyzed by "gating" based on the data collected for the entire population. To select an appropriate gate, the data is plotted so as to obtain the best separation of subpopulations possible. This is typically done by plotting forward light scatter (FSC) vs. side (i.e., orthogonal) light scatter (SSC) on a two dimensional dot plot. The flow cytometer operator then selects the desired subpopulation of cells (i.e., those cells within the gate) and excludes cells which are not within the gate. Typically, the operator selects the gate by drawing a line around the desired subpopulation using a cursor on a computer screen. Only those cells within the gate are then further analyzed by plotting the other parameters for these cells, such as fluorescence. While gating is a powerful tool for removing data for cells which are not of interest and thereby improving the ability to analyze the desired subpopulation, it can be a source of substantial error if separation of the subpopulations is not optimal.

Resolution of leukocyte subpopulations by light scattering is impaired when unlysed or whole blood samples are analyzed by flow cytometry. This is due to the fact that red blood cells (erythrocytes) present in the sample interfere with light scatter measurements and obscure signals from other cell types. Interference is particularly large for forward scatter, causing large errors in analysis of lymphocytes. For this reason, practitioners typically lyse the red blood cells in a sample when it is desired to analyze the leukocytes. Several reagents for lysing erythrocytes which are useful in the invention (e.g., water, saponin and the other lysing reagents discussed below) are known in the art. The most commonly used is buffered ammonium chloride. Although generally adequate separation of debris from lymphocytes using scatter gating in ammonium chloride solutions can be obtained, the absence of a fixative means the biological sample may present a biohazard. Addition of a fixative such as paraformaldehyde to ammonium chloride lysing solutions is unsatisfactory, however, due to generation of hydrogen ions which lower the pH of the sample and reduce fluorescence from fluorescein, thereby impairing immunofluorescence analysis.

Lysing reagents comprising formaldehyde, a salt of a weak acid and a polyhydric alcohol are also known in the art (U.S. Pat. Nos. 4,902,613 and 4,654,312). This lysing reagent is available from Becton Dickinson Immunocytometry Systems, San Jose, Calif. under the name FACS Lysing Solution and comprises diethylene glycol, heparin, citrate buffer and formaldehyde, pH 7.2. Because of the presence of formaldehyde, FACS Lysing Solution provides the advantage of reducing the biohazard from biological samples. However, its presence in a sample being analyzed by flow cytometry causes cell shrinkage and may result in unsatisfactory levels of debris which can obscure the cell population to be gated, particularly lymphocytes. Other lysing reagents known in the art are described below in connection with "no-wash" sample preparation methods.

To reduce the negative effect of lysing reagents on light scattering parameters the lysed sample is typically centrifuged and washed to remove debris, unbound fluorochrome-labeled antibodies and the lysing solution itself, all of which contribute to poor light scatter analysis. While this method partially solves the problem of resolving leukocyte subpopulations based on light scattering characteristics, it is labor intensive, adds steps to the procedure, is difficult to automate and can result in a loss of cells which precludes making accurate cell counts on the sample. For example, to obtain accurate CD4+lymphocyte counts from lysed, washed blood samples, presently available methods require multiple steps and complex data analysis.

It is therefore desirable to have methods available for preparation of lysed blood samples which do not require removal of the lysing solution and washing prior to low cytometric analysis. Such "no-wash" sample preparation methods for flow cytometry are known in the art. Caldwell, et. al (AJCP 86:600–607 (1986)) describe a no-wash method for immunophenotypic analysis of cells by flow cytometry in which lymphocytes are isolated from peripheral blood samples by fractionation on density gradients, obviating the need for erythrocyte lysis. After immunofluorescent staining, samples are subjected to flow cytometric analysis without washing, leaving unbound fluorescent label in the analyzed sample. Lymphocytes are identified and gated using forward and side light scatter parameters.

U.S. Pat. No. 5,030,554 discloses treatment of a blood sample with a lytic agent comprising a water soluble, organic carboxylic acid having a pK value greater than 3.0, a pH of about 2.6 to 4.0 and a counterion which does not materially alter the ionic strength of the sample. The separate staining, lysing and quenching steps are performed in a single vessel without the need for removal of unreacted stain and/or unconsumed reagents from the sample prior to analysis. The leukocyte subpopulations are identified and resolved in the traditional manner, using forward light scatter and side light scatter parameters. This no-wash method is commercially available from Coulter Corporation under the name Q-PREP. Ortho Diagnostic Systems has also published a no-wash sample preparation protocol using ammonium chloride which notes that if analysis of the cells in the lysing solution is not to be performed within 2 hours, the cells should be centrifuged, washed, resuspended in phosphate buffered saline and analyzed within 8 hours.

WO 88/07187 discloses a reagent for lysis of red blood cells which comprises a low molecular weight carboxylic acid, a sulfonic acid or an activated phenol. The lysed sample is directly analyzed by flow cytometry to identify leukocyte subpopulations based on forward and angular light scatter. It is taught that red cell fragments do not interfere with or adversely effect the photometric differentiation of leukocyte subpopulations using this lysing reagent.

Several methods for analyzing and gating leukocyte subpopulations are known in the art. U.S. Pat. No. 4,284,412 discloses an apparatus and method for gating a leukocyte subpopulation such as lymphocytes. A flow cytometer is modified such that one of the right angle-fluorescence channels serves as a wavelength specific sensor for right angle scatter. A lymphocyte subclass of interest is fluorescently labeled and the sample is analyzed, using detection of forward and right angle scatter pulses within specified ranges to actuate acquisition of a fluorescent signal, thereby gating the lymphocyte population. The apparatus and method are used in conjunction with lysis and washing of erythrocytes in the blood sample according to conventional procedures.

U.S. Pat. No. 4,727,020 discloses a method for analysis of subpopulations of blood cells using a fluorescence trigger and either lysed and washed or unlysed samples. The antibodies for use in triggering include anti-HLe-1 and the acquired data are analyzed using two fluorescence parameters to resolve the subpopulations.

Terstappen, et al. (J. Immunol. Mtds. 123:103–112 (1989)) describe a no wash method for flow cytometry sample preparation in which peripheral blood cells are labeled with the nucleic acid stain LDS-751. The red blood cells in the labeled sample are lysed in water prior to measurement on a flow cytometer. Immunofluorescence resolution of leukocytes and percentage of leukocyte subpopulations correlated well with results obtained with a clinical hematology analyzer and the nucleic acid stain allowed discrimination of intact cells from ghosts, platelets and damaged nucleated cells. The no-wash, hypotonic lysis procedure provided a means of obtaining absolute numbers of leukocyte subpopulations, whereas traditional lysis procedures which included centrifugation steps exhibited significant loss of cells and/or selective loss of lymphocyte subpopulations.

Gating methods which are not based solely on analysis of forward and side light scatter parameters are also known in the art. Hoffmann (Cytometry Supp. 1, pg. 36, Abstract No. 172 (1987)) describes the use of fluorescence to distinguish leukocyte subpopulations in unlysed blood samples, triggering on a fluorescence parameter and using light scatter to further differentiate leukocyte subpopulations. However, coincidence of erythrocytes with leukocytes partially obscured the right angle scatter distributions, providing suboptimal gating of lymphocytes. U.S. Pat. No. 4,987,086 discloses a method for determination of leukocyte subpopulations utilizing flow cytometry in which a gate is established by 1) labeling with a fluorochrome-labeled antibody which reacts with all leukocytes, and 2) labeling monocytes with a fluorochrome-labeled antibody specific for monocytes. This method is also taught by Loken, et al. (Cytometry 11:453–459 (1990)). To establish the gate, the cells are analyzed for forward light scatter and side light scatter as well as the two colors of fluorescence associated with the antibodies. A computer algorithm compares the light scatter data with the fluorescence analysis and differentiates those cells which should be included within the gate. The computer controlled gating analysis eliminates much of the subjectivity and error associated with visual gating methods. However, although the accuracy of the gating procedure is improved, this method has the disadvantage of requiring separate preparation of at least two sample aliquots and at least two separate flow cytometer runs for analysis of each sample (i.e., the gating tube and the experimental tube). This gating protocol is sold by Becton Dickinson Immunocytometry Systems under the name LEUCOGATE.

Horan, et al. (PNAS 83:8361–8365 (1986)) describe a method for analysis of leukocyte subsets in which five cell subsets are simultaneously identified using two-color immunofluorescence. The identification of subsets can be made with fluorochrome labeling of only a single aliquot of a sample, in contrast to prior art methods in which multiple aliquots of the same sample must be stained. Horan, et al. use dilutions of the fluorochrome-labeled antibody reagents to produce discrete fluorescence intensity profiles for cell subsets that would otherwise overlap or be indistinguishable when stained with antibodies bearing the same fluorochrome.

The present invention overcomes these problems in the art. It provides a method for establishing flow cytometry gates for leukocyte subpopulations under conditions where forward light scatter and side light scatter are unsatisfactory for this purpose. In one embodiment, multiple aliquots of a sample are stained with different fluorochrome-labeled antibodies for identification of multiple subsets of a subpopulation of interest. It is also possible using the inventive methods to perform gating and sample analysis on a single aliquot of sample with a single flow cytometer run, particularly in situations where information on the extent of myeloid cell contamination of the gated cells is not required.

The invention also provides a method for preparing a lysed blood sample for analysis of leukocytes by flow cytometry which does not involve centrifugation and washing of the stained and lysed sample prior to analysis on a flow cytometer. In the clinical laboratory setting, results are generally rejected for samples with less than 90% lymphocytes included in the gate. Using the inventive methods to trigger out debris, including much greater than 90% lymphocytes in the gate is more easily achieved. In addition, the inventive methods can be used to correct data from all samples with less than 90% lymphocytes gated when debris or nonlymphocyte cells are the source of the gating problem.

SUMMARY OF THE INVENTION

A method of flow cytometric analysis of leukocyte subpopulations is provided in which a fluorescence trigger is set instead of the customary forward scatter trigger. Leukocyte gates are established using light scatter and fluorescence analysis of blood cells stained with a fluorochrome conjugated to a monoclonal antibody which binds to a marker (i.e., an antigen) present on all leukocyte subpopulations. The leukocyte marker recognized by the fluorochrome-conjugated antibody is preferably present on each subpopulation in varying amounts to maximize differentiation of the subpopulations by their fluorescence intensity and light scattering properties. These methods provide improved separation of leukocyte subpopulations under conditions where resolution by light scatter parameters is unsatisfactory.

Elimination of most debris from data acquisition and analyses according to the invention can be performed directly on the sample being analyzed, eliminating the need for multiple tubes and multiple flow cytometry runs for analysis of a single sample. In lysed blood or bone marrow samples, gates can be established without the need for centrifuging and washing the blood sample after lysing, thereby reducing the number of sample processing steps and making it possible to obtain accurate absolute leukocyte counts without complex data analysis. If red cells in the blood sample are not completely lysed prior to analysis, light scatter/fluorescence gating provides resolution of the lymphocyte subpopulation without significant interference from erythrocytes in the sample.

DESCRIPTION OF THE DRAWINGS

FIGS. 2C and 2D are plots of log fluorescence (FL1, anti-Leu-M7-FITC vs. log fluorescence (FL2, anti-Leu-M3-PE) for the gating methods of FIG. 2A and FIG. 2B, respectively, showing the amount of non-lymphocytic contamination included in each gate.

FIG. 3A shows the R1 lymphocyte gate established by analysis of SSC/FSC parameters. FIG. 3B shows the R2 lymphocyte gate established by analysis of SSC/FL3 parameters. FIG. 3C shows an analysis of the FL1 and FL2 parameters of the R1-gated lymphocytes, demonstrating the myeloid nature of the contaminating non-lymphocytic cells. FIG. 3D shows an analysis of the FL1 and FL2 parameters of the (R1+R2) (i.e., 3-parameter) gated lymphocytes, demonstrating the reduction in contaminating myeloid cells by this method.

FIG. 4A shows analysis of lysed, washed blood samples gated on SSC/FSC. FIG. 4C shows the cell counts obtained by analysis of the sample in FIG. 4A. FIG. 4B shows analysis of lysed, washed blood samples gated on SSC/FL3. FIG. 4D shows the cell counts obtained by analysis of the sample in FIG. 4B. FIG. 4E shows analysis of lysed, washed blood samples containing residual erythrocytes gated on SSC/FSC. FIG. 4F shows analysis of lysed, washed blood samples containing residual erythrocytes gated on SSC/FL3. FIG. 4H shows the cell counts obtained by analysis of the sample in FIG. 4F.

FIG. 5A shows the classified lymphocytes after attractors analysis of the listmode data. FIG. 5B shows the four lymphocyte subpopulations identified by fluorescence.

DETAILED DESCRIPTION OF THE INVENTION

The present invention provides a method using flow cytometry for identifying and enumerating cells representing subpopulations of leukocytes in a biological sample containing leukocytes mixed with other blood cell types (e.g., blood or bone marrow samples). The method utilizes a fluorescence trigger to exclude selected subpopulations of blood particles prior to gating, and a gate established by analysis of acquired data parameters to exclude selected subpopulations of leukocytes from data analyses. A 2-parameter gate may be established based on analysis of a single light scattering parameter and a single fluorescence parameter (e.g., SSC and fluorescence). Alternatively, a 3-parameter gate may be established based on a combined analysis of SSC, FSC and fluorescence parameters.

For this purpose, a fluorochrome-labeled antibody which recognizes an antigen or marker associated with all leukocyte subpopulations (the "primary antibody") is used to stain the cells of the sample. The primary antibody is selected so that it binds to all leukocyte cell types but preferably with a detectably different intensity on each subpopulation. That is, the primary antibody is directed against a leukocyte antigen which is present in different amounts on each leukocyte subpopulation. The primary antibody does not bind to any significant degree to debris or to cell types other than leukocytes. The intensity of fluorescence characteristic of each leukocyte subpopulation, in combination with other measured parameters, therefore allows differentiation of the leukocyte subpopulations by flow cytometry. The primary antibody, because it binds substantially only to leukocytes, also allows discrimination between leukocytes and red cells, debris such as cell membranes (ghosts), platelets and other particles in the sample which exhibit minimal binding of the primary antibody.

After staining the sample with the primary antibody, and optionally with at least one secondary antibody as described below, it is analyzed on a flow cytometer, preferably without centrifugation or washing of the cells. The flow cytometer is preferably set with a trigger threshold on fluorescence emitted by the fluorochrome on the primary antibody. Light scatter and antibody fluorescence data are collected for each cell detected. A dot plot or histogram of the data is generated using primary antibody fluorescence (PAbF) and one of the light scatter parameters (FSC or SSC). The leukocyte subpopulation of interest is then identified on the plot and gated using methods known in the art.

Figure 1A:
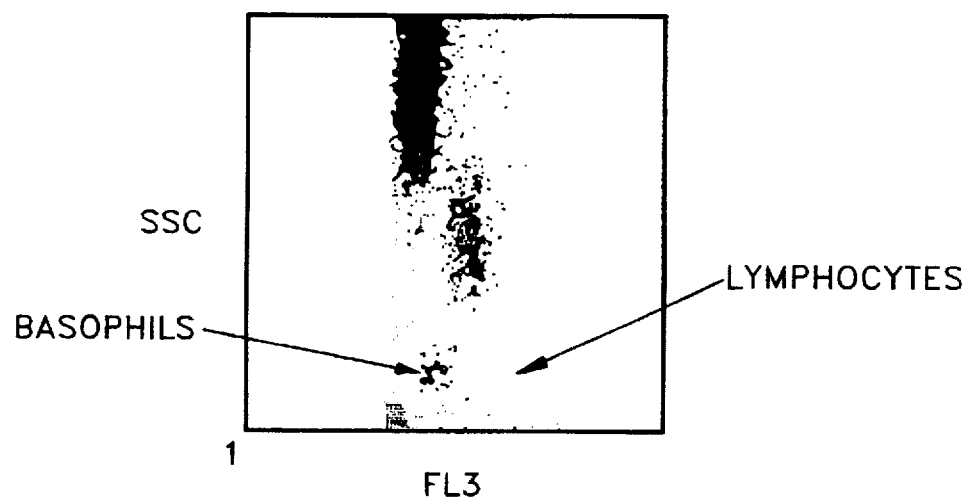
FIGS. 1A–1B illustrate the ability of the inventive method to resolve basophils from lymphocytes (FIG. 1A), whereas conventional scatter gating does not (FIG. 1B).
Figure 1B:
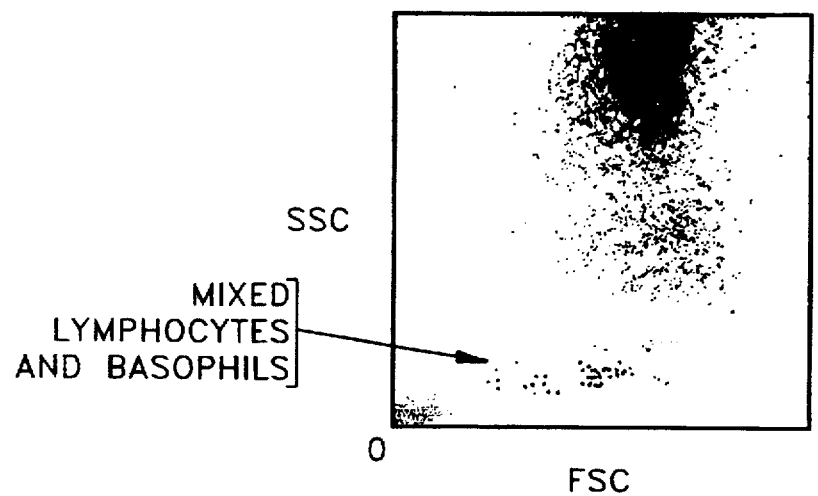
Figure 2A:
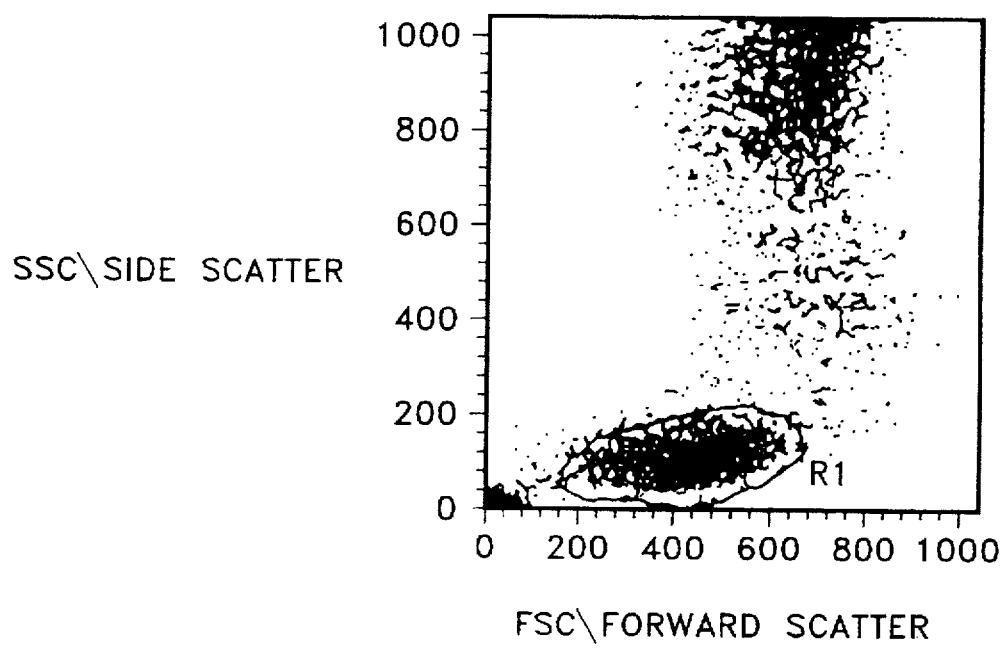
FIGS. 2A–2D illustrate 2-parameter gating according to the invention. Conventional FSC/SSC scatter gating (R1, FIG. 2A) is compared to the 2-parameter gating method of the invention (R2, FIG. 2B).
Figure 2B:
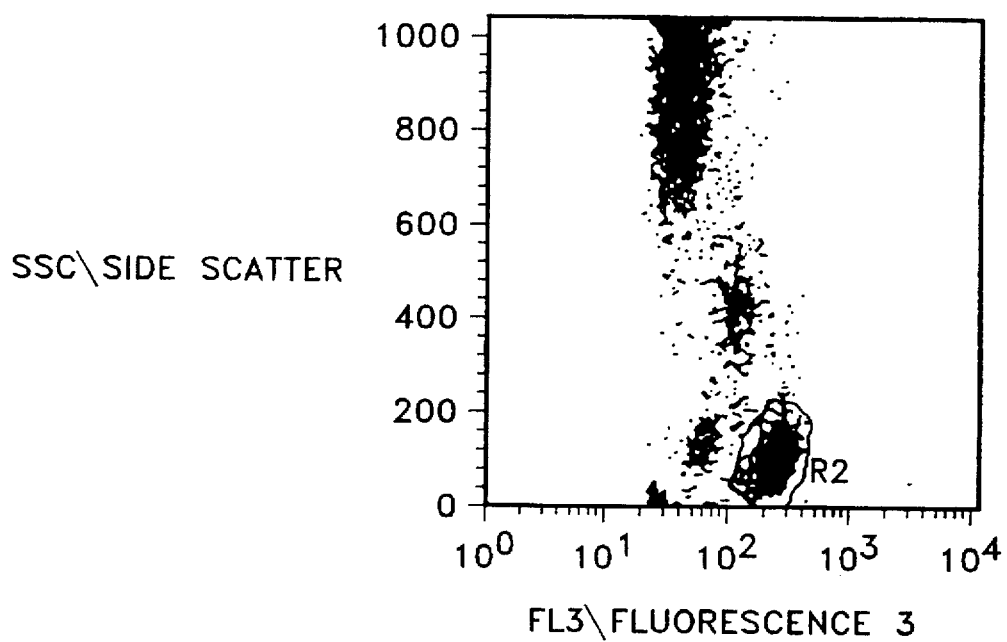
Figure 2C:
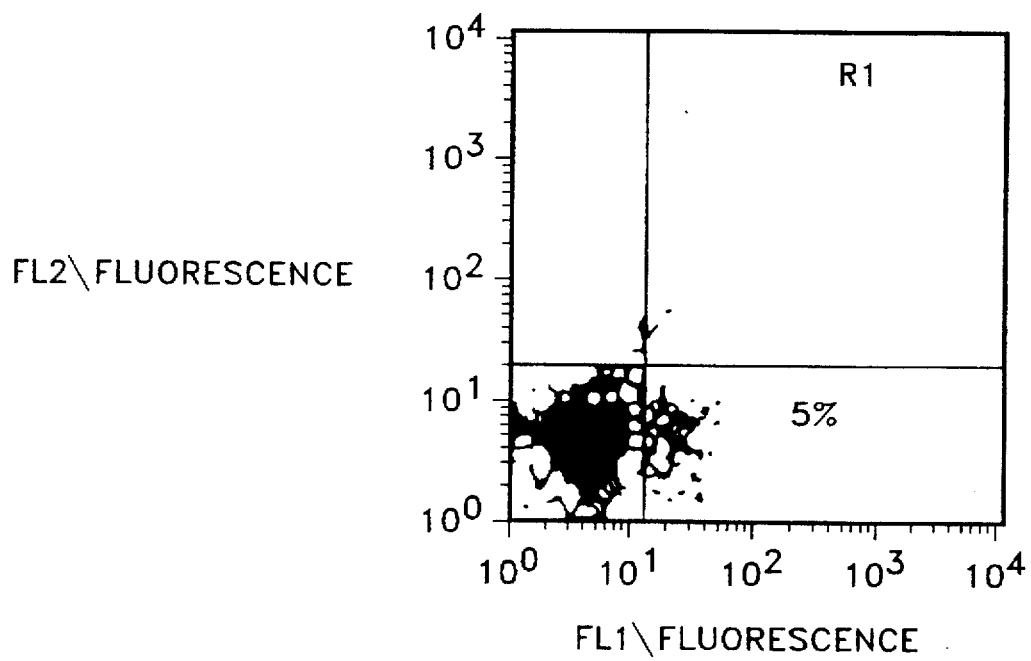
Figure 2D:
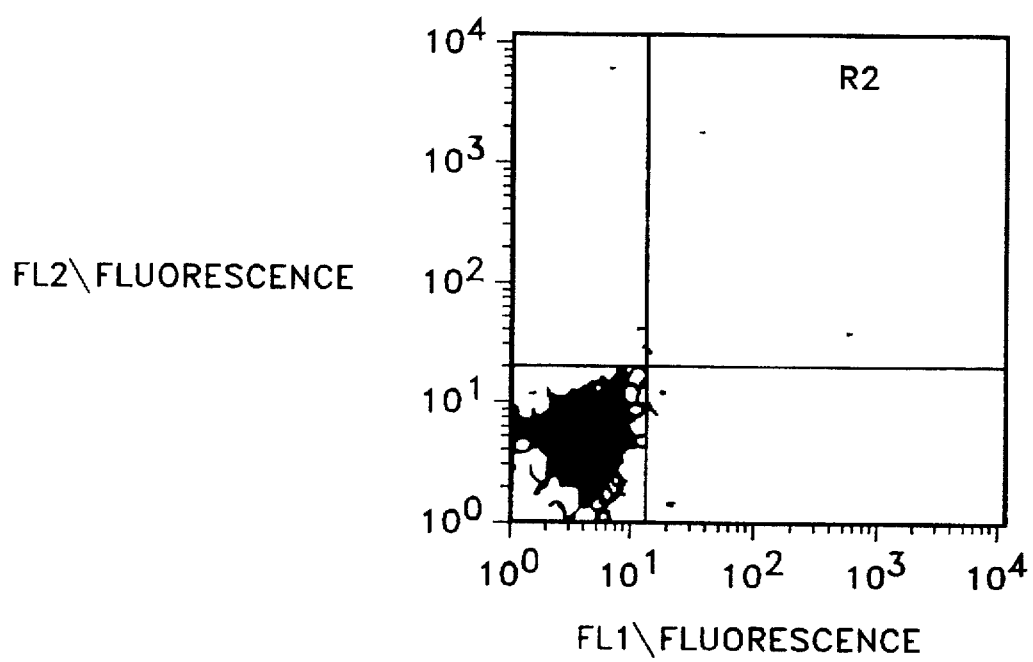

Although a conventional SSC/FSC analysis may be used to gate the desired leukocyte subpopulation, establishing the gate using scatter vs. PAbF (a 2-parameter gate) provides significantly improved resolution of the leukocyte subpopulations from platelets, debris, etc. It is also possible by this method to discriminate between lymphocytes and basophils which are usually inseparable from lymphocytes when gating by conventional methods of data analysis compare FIG. 1A and FIG. 1B. The inventive method therefore provides a means for eliminating basophil contamination from the lymphocyte gate using a 2-parameter light scatter/fluorescence gate, improving the purity of the gated lymphocytes.

Alternatively, a 3-parameter gate may be established for the acquired data to improve resolution of the various leukocyte subpopulations. Typically, a first gate (R1) is established by analysis of FSC vs. SSC and a second gate (R2) is established by analysis of SSC vs. PAbF. When plotted and analyzed in two dimensions the 3-parameter gate (R3) is based on an analysis of R1 and R2 to select only the cells contained in both gates. In general, a whole blood sample is incubated with at least two fluorochrome-labeled antibodies. One of these is the primary antibody described above. One or more additional fluorochrome-labeled antibodies (the "secondary antibodies"), specific for an antigen or cell type of interest, may also be included in the staining mixture to provide additional fluorescent signals for analysis. The fluorochromes on the secondary antibodies emit fluorescent light at wavelengths which are separately detectable and can be distinguished from each other and from primary antibody fluorescence by the flow cytometer. The primary and secondary antibodies may recognize and bind to the same or different antigens.

The fluorochromes useful for conjugation to antibodies according to the present invention may be any of the fluorochromes commonly used in flow cytometry which can be conjugated to proteins such as antibodies. Fluorescein isothiocyanate (FITC), phycoerythrin (PE), and peridinin chlorophyll protein (PerCP) are preferred because they can be excited by light of the same wavelength but emit light at separately detectable wavelengths compatible with flow cytometric analysis. Any of these fluorochromes can be used to label the primary and secondary antibodies of the invention using conjugation methods well known in the art. See, for example, U.S. Pat. No. 4,876,190 and references cited therein for a discussion of covalent and noncovalent conjugation of fluorochromes to proteins such as antibodies. The disclosure of U.S. Pat. No. 4,876,190 is incorporated herein by reference.

The primary and secondary antibodies may be polyclonal or monoclonal, but are preferably monoclonal antibodies. The primary antibody may be any antibody capable of binding to the entire cell population of interest with minimal binding to other cell types. Preferably leukocytes are bound by the primary antibody. Such anti-leukocyte monoclonal antibodies are known in the art and include, but are not limited to, CD45 (e.g., anti-HLe-1) and CD11a/CD18 (e.g., anti-LFA-1). The fluorochrome label on the primary antibody is not critical but is preferably FITC, PE or PerCP.

CD45 conjugated to PerCP, which will bind to and identify leukocytes, is the most preferred primary antibody for use in the invention. CD45 has the advantage of being able to bind to fixed cells, allowing staining after lysis and fixation if desired, for example when the method of the invention is used to correct a previous gate which gave unsatisfactory results.

Secondary antibodies, labeled with a fluorochrome different from the fluorochrome on the primary antibody, may also be either polyclonal or monoclonal antibodies. Monoclonal antibodies are preferred for their enhanced specificity. The secondary antibodies are selected to be specific for and to bind to any antigen for detection of any cellular characteristic of interest to the investigator. Secondary antibodies may be used to identify either the gated subpopulation of cells (e.g., lymphocytes) or a subset of the subpopulation (e.g., T cells or B cells). If desired, the secondary antibody may comprise the same antibody used to identify the subpopulations (i.e., the antibody component of the primary antibody) but bound to a different fluorochrome than is used for the primary antibody so that it can be separately detected. For example, CD4 (e.g., anti-Leu-3a) may be used as secondary antibodies to detect helper/inducer T lymphocytes, CD8 (e.g., anti-Leu-2a) may be used to detect cytotoxic/suppressor T lymphocytes, CD14 (e.g., anti-Leu-M3) may be used to detect monocytes, CD13 (e.g., anti-Leu-M7) may be used to detect myeloid cells, CD3 (e.g., anti-Leu-4) may be used to detect T lymphocytes, and CD19 (e.g., anti-Leu-12) may be used to detect B lymphocytes. All of these antibodies as well as CD45 are available from Becton Dickinson Immunocytometry Systems, San Jose, Calif. CD56 (e.g., anti-Leu-19 or anti-NCAM), CD57 (e.g., anti-Leu-7), CD38 (e.g., anti-Leu-17), CD28 and anti-HLA-DR are also useful as components of secondary antibodies for certain applications in the practice of the invention. In addition, CD14 and CD13 can be used as quality control agents to assess the purity of the gated lymphocytes.

Other antibodies may be useful for detecting leukemic cells in blood samples according to the invention. For example, leukocytes may be stained using a primary antibody comprising a CD45 antibody and a secondary antibody comprising an antibody specific for leukemic cells of interest. Alternatively, a blood sample may be analyzed as described above, and if the initial results suggest an abnormality, the sample may be restained with secondary antibody which will bind to and specifically detect leukemic cells.

The particular fluorochrome selected as a component of the secondary antibody is not critical but is preferably FITC, PE, or PerCP. PE and/or FITC are most preferred for labeling the secondary antibody when PerCP is the fluorochrome on the primary antibody.

To label cells in the sample by binding to the primary and/or secondary antibodies, a sample such as whole blood or bone marrow is mixed with the fluorochrome-labeled primary and secondary antibodies. The labeled antibodies are generally added to the sample substantially simultaneously and mixed therewith. Cell labeling methods suitable for use in the invention are well-known in the art. For flow cytometry, the blood or bone marrow sample will generally be about 100 µl in volume and about 0.05–1.0 µg of each antibody will be added per sample. After addition of the desired labeled antibodies, the sample is incubated at room temperature, preferably in the dark, for about 5–30 min. For most applications, an incubation period of about 15 min. is generally sufficient to obtain satisfactory binding. It is generally possible to use less secondary antibody in the staining procedures of the invention (up to about a 20-fold reduction) than is typical for samples which are to be washed, because bound antibody is not washed off.

If erythrocytes in the labeled sample are to be lysed prior to flow cytometric analysis, a lysing reagent is added to the labeled sample. Lysing reagent may be added to the sample with the labeled antibodies or lysis may be performed prior to labeling. However, labeling the cells first with subsequent lysis of erythrocytes is preferred to maximizing binding of the antibodies. The sample is incubated in the presence of lysing reagent for about 10 min. Suitable lysing reagents for this purpose may include, but are not limited to, ammonium chloride and FACS Lysing Solution.

FACS Lysing Solution is preferred because it provides better lymphocyte/monocyte separation on side scatter than does ammonium chloride, provides stable light scatter and fluorescence results for extended periods of time, and allows lysing and fixing to be performed in a single step. A sample of stained, unwashed blood in FACS Lysing Solution generally remains stable for up to 48 hrs., and in some instances the light scatter even improves with increasing incubation time. In addition, the relatively high concentration of formaldehyde (3%) in FACS Lysing Solution may provide a higher degree of biosafety than other lysing reagents.

Because the presence of some erythrocytes in the sample does not significantly interfere with the gating method of the invention, for purposes of gating and flow cytometric analysis it is not necessary that all erythrocytes in the sample be lysed. It is therefore possible to use less lysing reagent than is customary for lysing methods which require that the sample be centrifuged and washed. For example, 2 ml of FACS Lysing Solution is generally added to a 100 µl blood sample. For use with the present methods, 0.5–1.0 ml of FACSTM Lysing Solution in 100 µl of blood gives satisfactory results on gating and flow cytometric analysis. Because there is reduced interference from red blood cells the invention will also provide better results for samples which contain erythrocytes which do not readily lyse under standard conditions (e.g., samples containing nucleated red blood cells). In some cases it may also be possible to analyze unlysed blood using the methods of the invention.

The fluorochrome-labeled sample is analyzed on a flow cytometer. If the sample is lysed prior to analysis, it is analyzed in the lysing reagent without removal of the lysing reagent, centrifugation or washing. Any of the commercially available flow cytometers which are capable of light scatter and at least two-color fluorescence data acquisition may be used for this purpose. Flow cytometers which are capable of acquiring at least three-color fluorescence data are preferred because after triggering and gating using one fluorescence parameter according to the invention, two-color analysis of the cells of interest can still be performed. One example of such an instrument is the FACSCAN available from Becton Dickinson Immunocytometry Systems. As the inventive method is also applicable to analyses involving detection of four or more fluorescence parameters, instruments such as the FACSTAR PLUS may also be used. This flow cytometer has two lasers which produce light of different wavelengths and is capable of detecting five fluorescence parameters and two light scatter parameters. Such an instrument provides a particular advantage for use in the invention as it allows use of a fluorescence parameter for triggering and gating while retaining the capability to perform three (or more)-color fluorescence analysis of the cells of interest.

The flow cytometer should produce light of an appropriate wavelength for excitation of the selected fluorochromes. Acquisition of FSC, SSC, and all fluorescence data for the cells in the sample is triggered by fluorescence of the fluorochrome selected for labeling the primary antibody. Triggering on the bright PAbF events serves to exclude the majority of debris and platelet events as well as other events which are not due to leukocytes. All of these non-leukocyte events can interfere with FSC resolution if they are not excluded. The acquired data is stored electronically and converted by computer using an appropriate algorithm to data which can be plotted in the form of a dot plot for gating.

For two-parameter gating, the data plot is preferably generated using light scatter vs. fluorescence. This method is illustrated in FIGS. 2A–2D. Most preferably the light scatter parameter is side scatter (SSC), but forward scatter (FSC) data may also be used. Any of the fluorescence parameters, as appropriate for the application, may be used as the second parameter. Primary antibody fluorescence is preferred (PAbF). The scatter vs. fluorescence dot plot is used to gate the desired cell subpopulation. Gating may be accomplished by any of the art-recognized methods using algorithms compatible with the flow cytometer used for sample analysis. For example, SIMULSET, LYSYS or PAINT-A-GATE data analysis software (Becton Dickinson Immunocytometry Systems) can be used to gate and analyze data acquired on the FACSCAN flow cytometer. Once the acquired data is gated, light scatter and fluorescence data acquired for the gated subpopulation can be analyzed on dot plots, histograms, contour plots or by other means known in the art.

Alternatively, a 3-parameter gate may be established for the acquired data to further improve resolution of the various leukocyte subpopulations and eliminate contamination from the gate. This method is illustrated in FIGS. 3A–3D. R1 may be established first by analysis of SSC and FSC with R2 established subsequently by analysis of SSC and PAbF. However, R1 and R2 may be reversed, establishing R1 first by analysis of SSC and PAbF and R2 second by SSC and FSC. A computer algorithm then compares R1 and R2 and establishes R3 to include the cells contained in both the R1 and R2 gates. The 3-parameter gating of the present invention, with appropriate software, also allows three-dimensional plotting and analysis of the three parameters. Such three-dimensional plotting and/or gating significantly improves resolution of all five leukocyte subpopulations (lymphocytes, monocytes, neutrophils, basophils and eosinophils) and therefore can allow calculation of a five part differential blood count using flow cytometry. Although currently available single-threshold instruments can perform such analyses, a flow cytometry instrument with dual-threshold capability would be more desirable for this purpose, as it would reduce debris and the number of cells that would have to be analyzed to obtain a reliable result.

Addition of the primary antibody of the invention to gating procedures known in the art, such as LEUCOGATE, with triggering on FL3 significantly reduces acquisition of debris in lysed unwashed blood samples and improves resolution of leukocyte subpopulations. This improvement is possible without reducing the number of fluorescence parameters which are available for data acquisition and analysis since trigger fluorescence need not be stored and treated as data. This is a particular advantage when using software in which the number of fluorescence parameters which can be analyzed is limited. For example, a lysed unwashed aliquot of a sample to be analyzed can be stained or labeled according to the standard LEUCOGATE procedure using an anti-leukocyte antibody conjugated to a first fluorochrome and an anti-monocyte antibody conjugated to a separately detectable second fluorochrome (e.g., anti-HLe-1-FITC and anti-Leu-M3-PE). The aliquot is also labeled with an anti-leukocyte primary antibody according to the invention comprising a third fluorochrome which can be differentiated from the first and second fluorochromes (e.g., anti-HLe-1-PerCP). The aliquot is then run on a flow cytometer set to trigger on FL3 (PerCP).

If it is desired to have available all of the fluorescence parameter analysis capability of the software, FL3 data are not stored. For example, SIMULSET software is limited to analysis of two fluorescence parameters and two light scatter parameters. To avoid limiting the system to analysis of a single fluorescence parameter in addition to the trigger, FL3 data (i.e., the trigger) would not be stored, leaving two fluorescence parameters available for data analysis. Data for the remaining two fluorescence parameters (FL1 and FL2) and the light scatter parameters are acquired and stored for particles exceeding the threshold and the gate is established by the software. This is the conventional SSC/FSC scatter gate when using SIMULSET. The gate established by this procedure is then applied to data obtained for a test aliquot of the sample labeled with the same primary antibody for triggering and any additional antibodies desired for flow cytometric analysis.

In the single-tube analysis format of the invention, the method provides a means for obtaining a maximum amount of information with minimal sample manipulation, resulting in time savings both in sample preparation and instrument data acquisition. It is therefore particularly suited for use in clinical laboratories which require high-throughput diagnostic products for tests such as routine lymphocyte enumeration. In a preferred embodiment, the present no-wash analysis method is used to obtain a three-part differential blood count (T, B and NK cells) with T-cell subsetting into CD4 (helper) and CD8 (suppressor) in a single tube flow cytometric analysis. The method allows detection of two or more subpopulations of leukocytes for each chromophore, for example using FITC and PE two-color fluorescence on a FACScan.

For example, for a three-part differential analysis with CD4/CD8 subsetting, FSC and SSC data are acquired for the sample as well as fluorescence data for the fluorochrome-labeled antibody combinations as follows:

| PARAMETER | ANTIBODIES | FLUOR |
| --- | --- | --- |
| FL1 | CD3 + CD4 | FITC |
| FL2 | CD8 + CD56 | PE |
| FL3 | CD45 | PerCP |

A single aliquot of blood is stained and lysed without washing and analyzed on the flow cytometer, triggering on CD45 PerCP fluorescence as previously described. B cells are presumptively identified as CD8−, CD56−, CD3−, CD4− cells (i.e., in the lower left area of a dotplot). NK cells are identified as CD8+, CD56+, CD3−, CD4− cells (i.e., in the upper left area of a dotplot). NK cells may also be identified by adding CD16 to CD8+56, as a small subset of NK cells are CD16+, CD56+. Cytotoxic suppressor T cells are identified as CD8+, CD56−, CD3+, CD4− cells (i.e., in the upper right area of a dotplot). Helper T cells are identified as CD8−, CD56−, CD3+, CD4+ cells (i.e., in the lower right area of a dotplot).

A two or three parameter gate may be set for the lymphocytes as previously described using any manual or automated means known in the art. It is preferred, however, that an autoclustering method capable of identifying subpopulations in multi-dimensional or N-dimensional space be used to automatically assign cluster classifications to the multiparameter events recorded during data acquisition. Such an autoclustering method is disclosed in PCT Application US 92/07291, filed Aug. 28, 1992, the disclosure of which is hereby incorporated by reference. The gravitational attractor described consists of a geometric boundary surface of fixed size, shape and orientation but with variable position. It is a computational engine by which the boundary surface positions itself optimally to enclosed a cluster of multi-parameter events. Classification of events in the listmode data acquired is a two step process in which 1) the datastream is analyzed for purposes of centering each attractor's boundary surface on the statistical center-of-mass of the data cluster it is intending to classify, and 2) locking each attractor's boundary in place and testing incoming datastream events against the boundaries for inclusion vs. exclusion decision-making. Such autoclustering methods are preferred over manual methods and previously know autoclustering methods for data analysis because they 1) allow analysis of data in real-time, 2) are tolerant of between-sample drift in the center-of-mass value of a data cluster due to changes in instrumentation, sample preparation and intrinsic sample variation, 3) are stable in cases where clusters are missing and 4) allow continuous process quality assurance during time-consuming rare-event assays. Using the inventive lysing, no-wash methodology with CD45-PerCP trigger and "Attractors" software as described in PCT Application US 92/07291, the practitioner can develop and analyze 100% of the lymphocytes without contamination by debris, platelets or myeloid cells.

The compositions and methods set forth herein represent certain embodiments of the principles of the invention. It is to be understood that the present invention may be embodied in numerous alternative fashions and that such alternative embodiments may be conceived by those skilled in the art using only routine abilities and without departing from the spirit and scope of the invention. Specific illustrative embodiments are set forth in the following Examples but are not to be considered as limiting the scope of the invention as defined by the appended claims and their equivalents.

EXAMPLE 1

No Wash Sample Analysis with 2-Parameter Gating

A whole blood sample (100 µL) was mixed with 0.25 µg HLe-1-PerCP antibody, 0.1 µg Leu-4-FITC antibody and 0.25 µg Leu-11+19-PE antibody (Becton Dickinson Immunocytometry Systems, San Jose, Calif.). The PE conjugates were processed by cation exchange and sizing by gel filtration to remove all detectable free PE and multiples (2:1 and 1:2 conjugates) so that greater than 90% of the product had a PE:Ig ratio to 1:1. This process improved performance of the no-wash reagents, possibly due to the tendency of free PE to stick nonspecifically to platelets which are by definition present in a no-wash sample. The inventive no-wash sample preparation required as much as 20-fold less PE for staining when a high proportion of 1:1 conjugates were used and resulted in reduced background fluorescence.

The mixture was incubated 15 min. at room temperature in the dark. Two ml of FACS Lysing Solution (Becton Dickinson Immunocytometry Systems) were added to the stained sample and it was incubated for 10 min. at room temperature in the dark. The lysed, labeled sample was then analyzed on a FACSCAN flow cytometer, triggering on FL3 (anti-HLe-1-PerCP) and acquiring fluorescence and light scatter data with CONSORT 32 software. Analysis of the acquired data was performed using FACSCAN Research, LYSYS II or SIMULSET software.

FIG. 2A–D shows a comparison of lymphocyte gating on SSC vs. FL3 to lymphocyte gating on SSC vs. FSC (FIG. 2A) for the unwashed, lysed sample. Gating on SSC vs. FL3 (FIG. 2B) significantly reduced the amount of debris included in the gate, as is shown in the plot of FL1 vs. FL2 for the gated leukocyte subpopulation compare FIG. 2C and FIG. 2D. Debris can be reduced as much as 50% using SSC vs. FL3 to establish the gate as compared to the traditional SSC/FSC gate. Triggering on FL3 allows acquisition of a greater number of analyzable cells in situations where a fixed number of events is being acquired since events which may be detected by scatter but are below the fluorescence threshold are not counted. Under certain experimental conditions, triggering on fluorescence may also improve the speed of data acquisition.

EXAMPLE 2
No Wash Sample Analysis with 3-Parameter Gating

Whole blood samples for eleven subjects (four 100 μL aliquots for each subject) were prepared on the FACSPREP, staining with 20 μL of anti-HLE-1-PerCP, anti-Leu-M7-FITC and anti-Leu-M3-PE (Becton Dickinson Immunocytometry Systems). Samples were incubated for about 15 min. at room temperature in the dark. Following labeling, 2 ml. of FACS Lysing Solution was added to each sample. These samples were analyzed on the FACSCAN without removal of the lysing solution or centrifugation and washing. These aliquots were analyzed triggering on FL3 (PerCP) and the data acquired in LYSYS for three-color analysis, gating the lymphocyte subpopulation.

No-wash data was analyzed using (1) LYSYS II with the conventional FSC/SSC scatter gate (R1) and a manually set FL3 trigger, and (2) LYSYS II with a manually set FL3 trigger and a 3-parameter gate based on SSC vs. FSC (R1) and SSC vs. FL3 (R2);

For comparison, two additional 100 μL aliquots of each sample were prepared on the FACSPREP, staining with SIMULTEST reagent kits (Becton Dickinson Immunocytometry Systems) according to the manufacturer's instructions, including centrifuging and washing the samples after lysing. These aliquots were analyzed on the FACSCAN with conventional triggering on light scatter. Data was acquired in SIMULSET software (Becton Dickinson Immunocytometry Systems) for two-color analysis, gating the lymphocyte subpopulation. For one washed sample the gate was set automatically by the software and for the second the gate was set manually by the operator.

In the washed samples using SIMULTEST staining, SIMULSET software and a light scatter trigger the two gating methods failed to eliminate debris from the gated lymphocyte subpopulation (1–8% contamination). There was some improvement in the quality of the gate when the operator redefined the gates. These gated lymphocyte subpopulations were also contaminated with 0–1% monocytes and 1–8% granulocytes.

In contrast, in the no-wash aliquots triggering on FL3 was effective to eliminate debris from the lymphocyte gate to levels below the detection limits of the analysis system, regardless of the method of data acquisition and gating. Monocytes were also eliminated from the gate in the no-wash format, regardless of whether the scatter gate or the 3-parameter gate was applied. Contamination of the gated lymphocyte population by granulocytes was significantly reduced by 3-parameter gating (0.2% average contamination), whereas the light scatter lymphocyte gate included between 1% and 6% granulocytes (probably primarily basophils). The 3-parameter gating method, in contrast to conventional 2-parameter light scatter gating, allows the operator to include essentially 100% lymphocytes in the gate with, on the average, no debris, no monocytes and only 0.2% granulocytes.

Figure 3A:
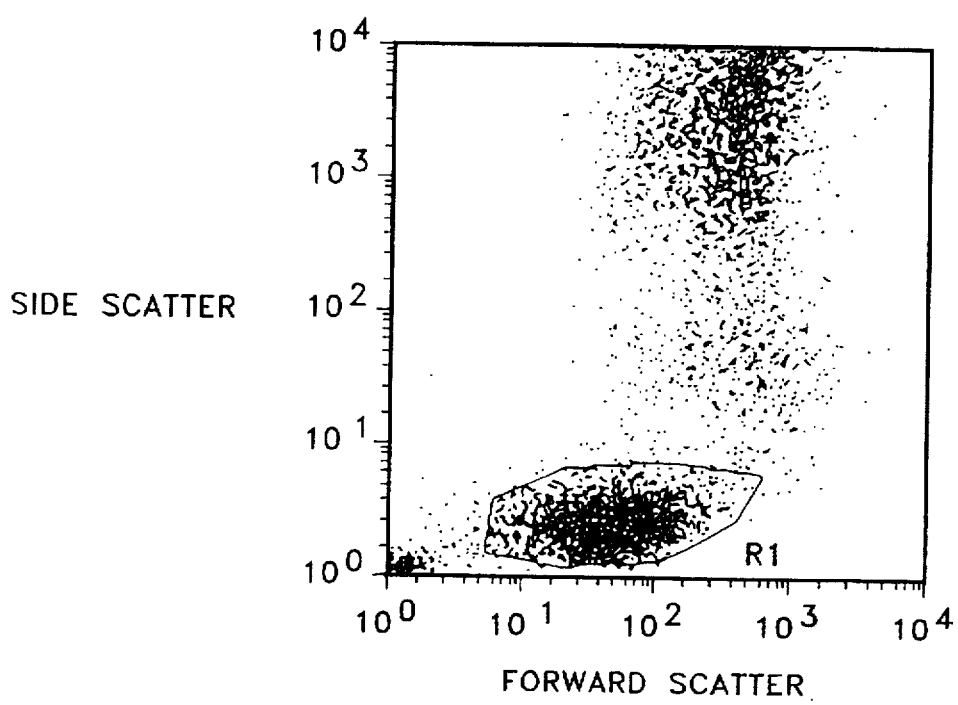
FIGS. 3A–3D illustrate 3-parameter gating according to the invention.
Figure 3B:
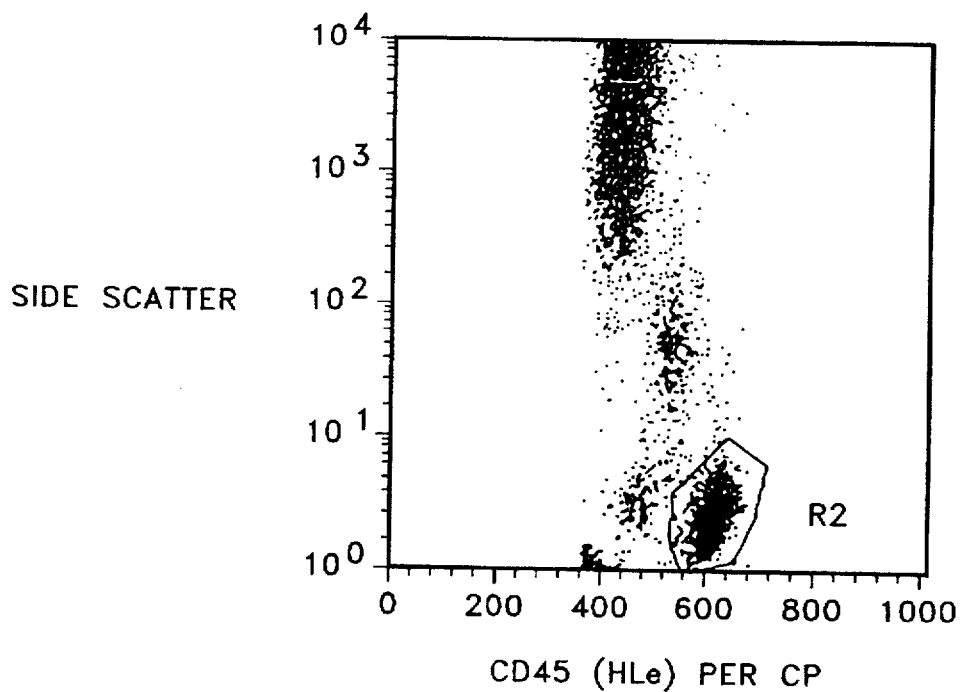
Figure 3C:
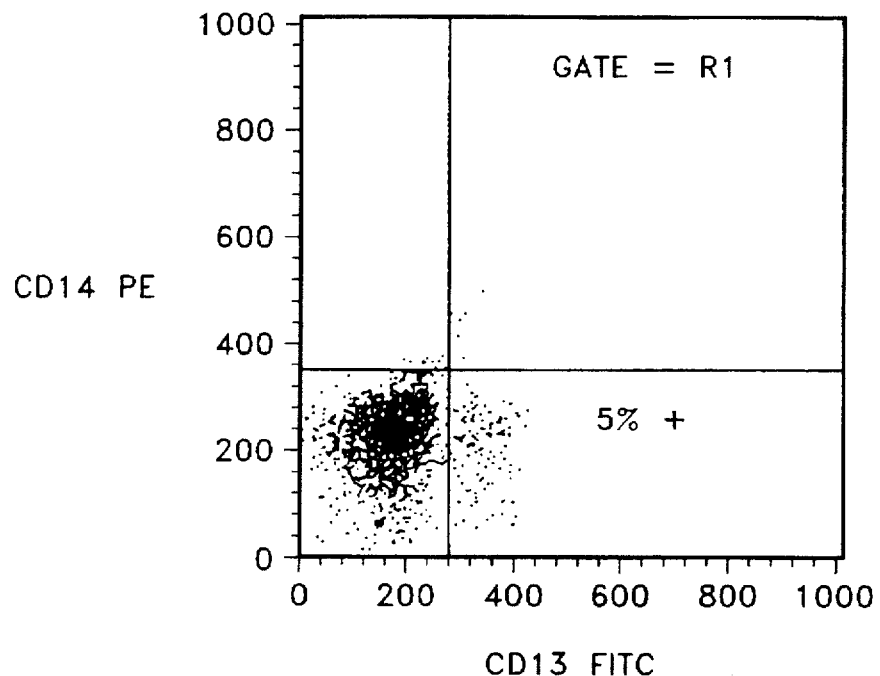
Figure 3D:
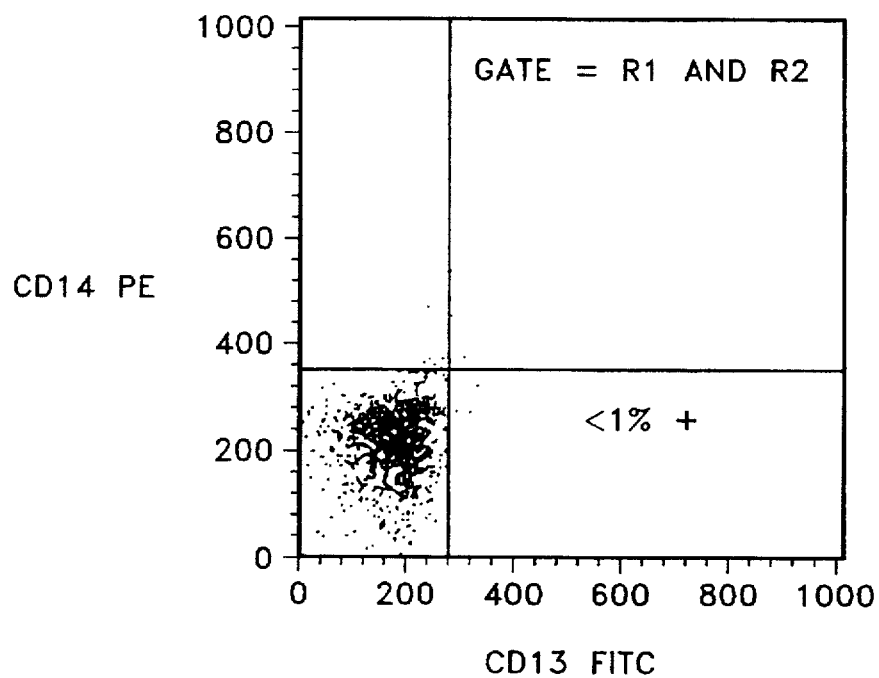

3-parameter gating is illustrated in FIG. 3A–D. R1 (FIG. 3A) and R2 (FIG. 3B) are established and the cells included in both are identified to form R3 (FIG. 3D). The improved purity of the 3-parameter gate can be seen by comparing FIG. 3D with FIG. 3C, which illustrates R1 alone (conventional SSC/FSC gate but with an FL3 trigger). Staining of the gated lymphocytes with anti-Leu-M3 and anti-Leu-M7 quantitates the comparative degree of contamination with myeloid cells using the two gating methods. As the Figures show, contamination of gated lymphocytes by myeloid cells is significantly reduced by 3-parameter gating.

EXAMPLE 3
Analysis of Blood Samples Cpntaining Erythrocytes

Figure 4A:
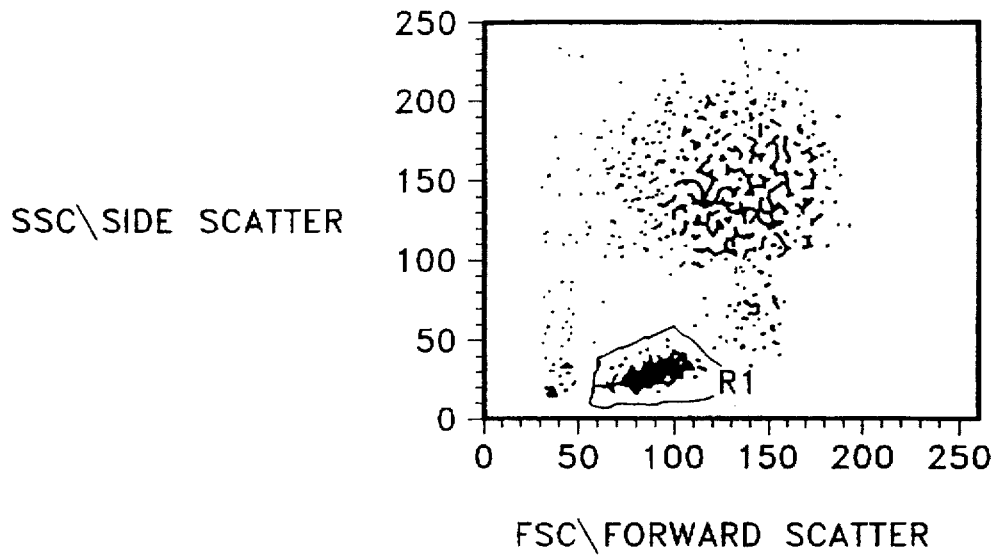
FIGS. 4A–4H illustrate the ability of the gating method of the invention to provide accurate cell counts even when lysed blood samples contain residual red blood cells.
Figure 4B:
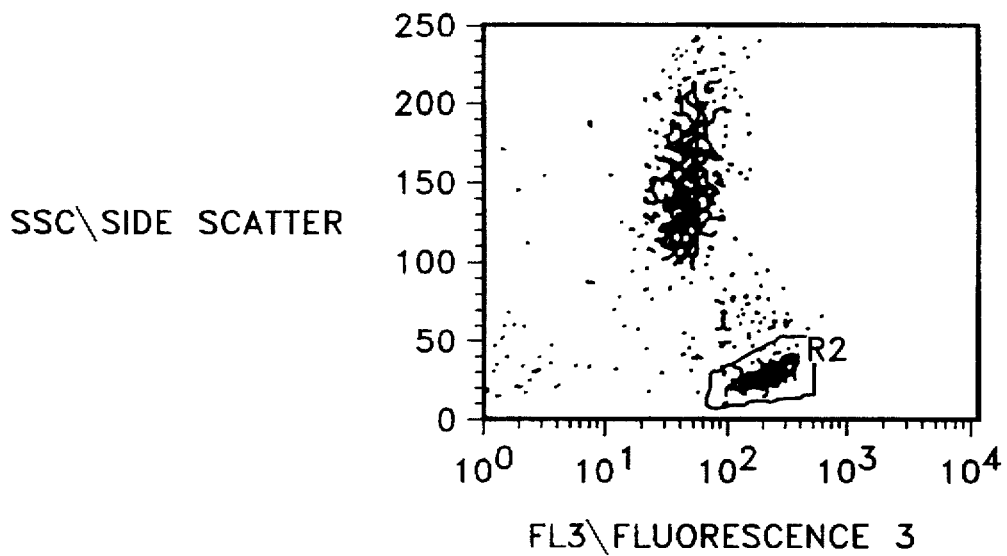

A blood sample was stained with anti-Leu-3a-PE, anti-Leu-2a-FITC and anti-HLe-PerCP, lysed with ammonium chloride, centrifuged and washed once with phosphate buffered saline. The sample was then split and red blood cells were added to one aliquot in sufficient quantity that about 70–80% of the events included in the gate were due to RBC's. The aliquots were analyzed on a FACSCAN flow cytometer and lymphocyte gates were set using SSC vs. FSC (FIGS. 4A and 4E) and SSC vs. FL3 (PerCP) (FIGS. 4B and 4F). FL1 and FL2 events were then plotted and counted for the gated lymphocytes.

Figure 4C:
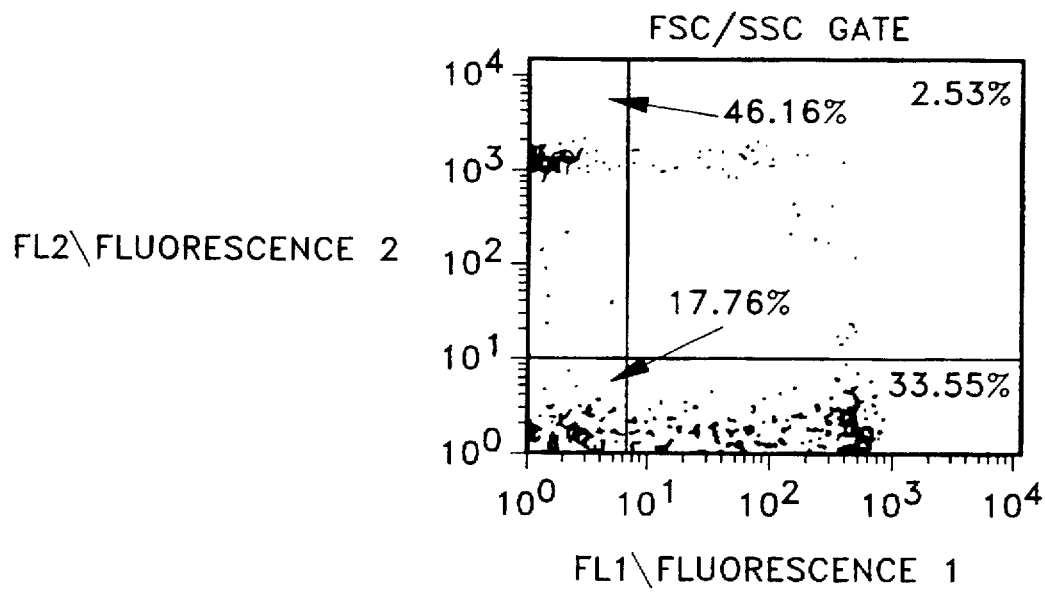
Figure 4D:
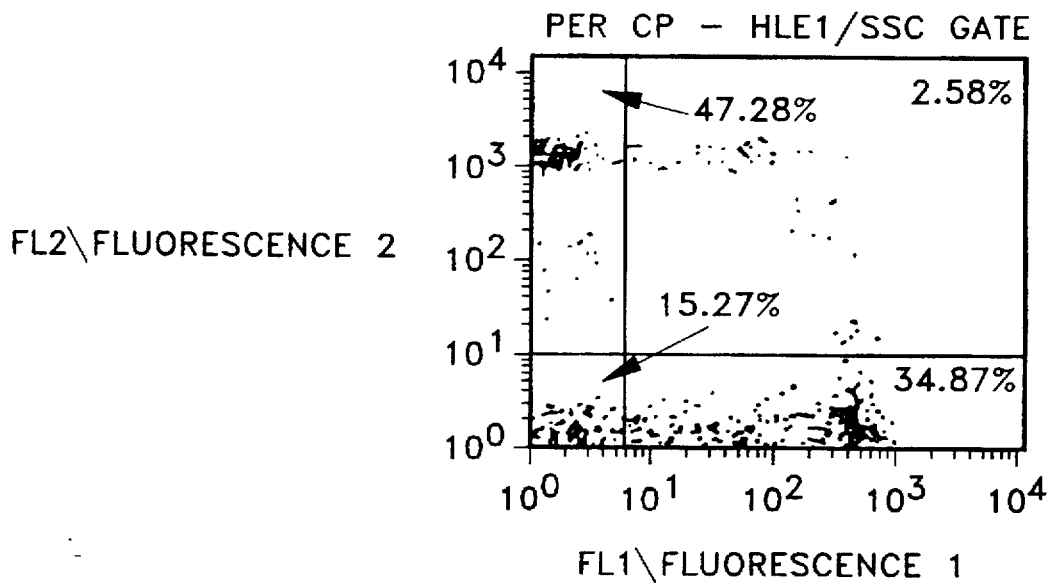
Figure 4E:
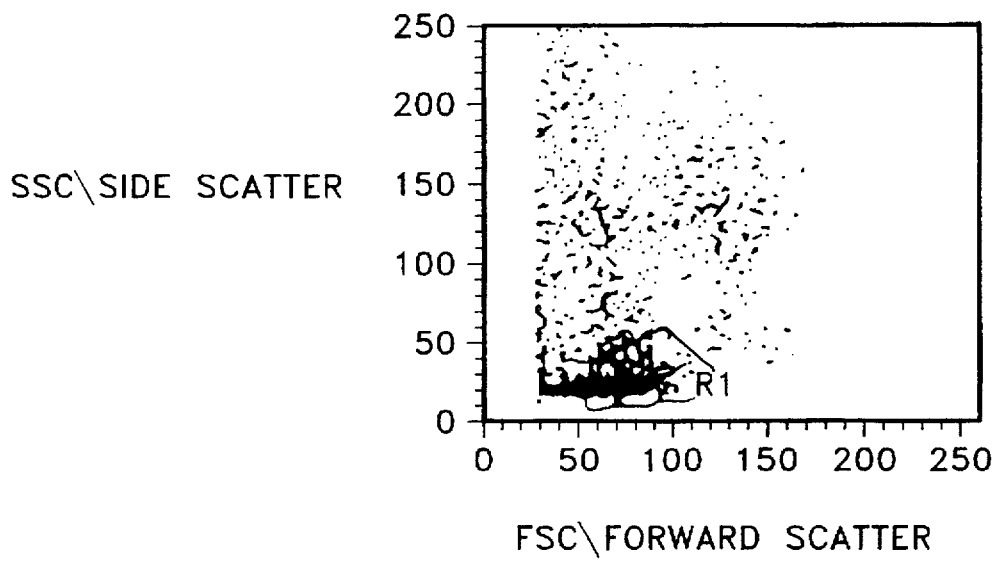
Figure 4F:
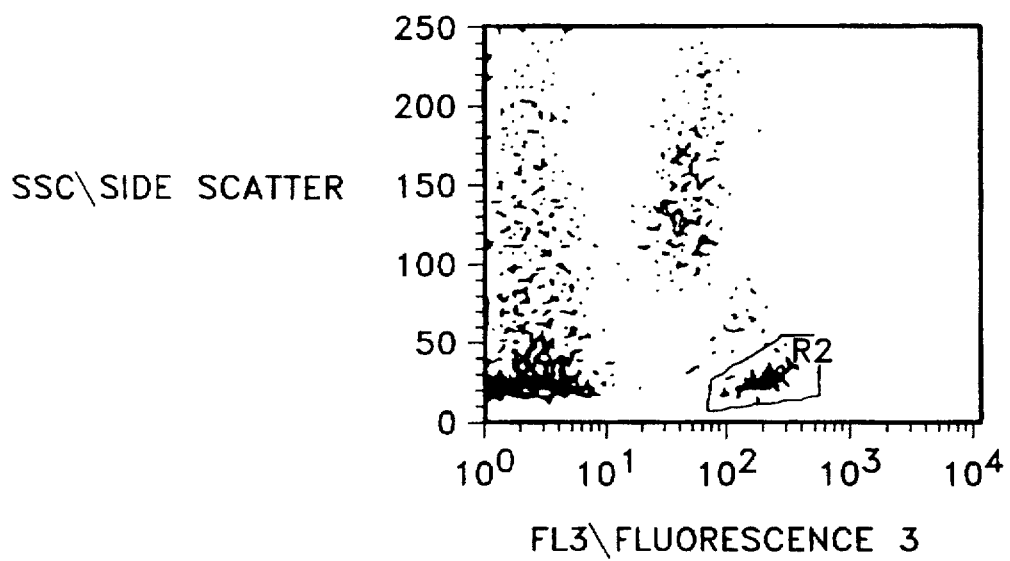
Figure 4G:
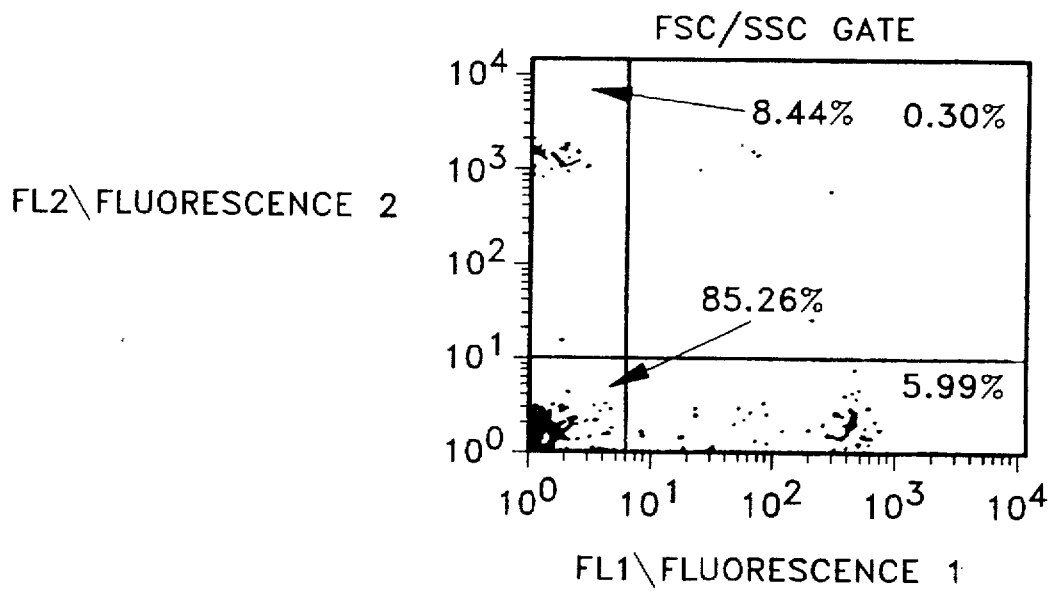
Figure 4H:
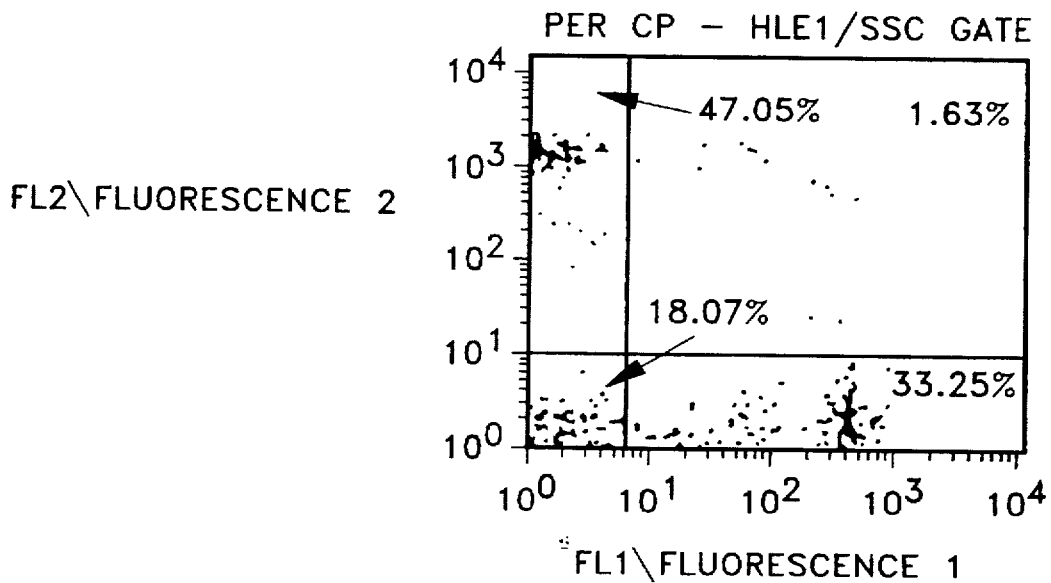

In the aliquot without added red blood cells, there was essentially no difference in the percentage of Leu-3a and Leu-2a positive cells with the two gating methods (compare FIG. 4C and FIG. 4D). In the aliquot containing red blood cells, accurate Leu-3a positive and Leu-2a positive percentages were obtained using SSC vs. FL3 gating, but SSC vs. FSC gating produced highly inaccurate results (FIG. 4H and FIG. 4G, respectively).

These results demonstrate that the present gating method does not result in loss of any cell populations as compared to conventional scatter gating. In addition, the method provides a means for compensating for light scatter interference from red blood cells in unlysed blood samples and lysing reagents in no-wash blood sample preparation methods.

EXAMPLE 4
Three-Part Differential with CD4/CD8 Subsetting

Figure 5A:
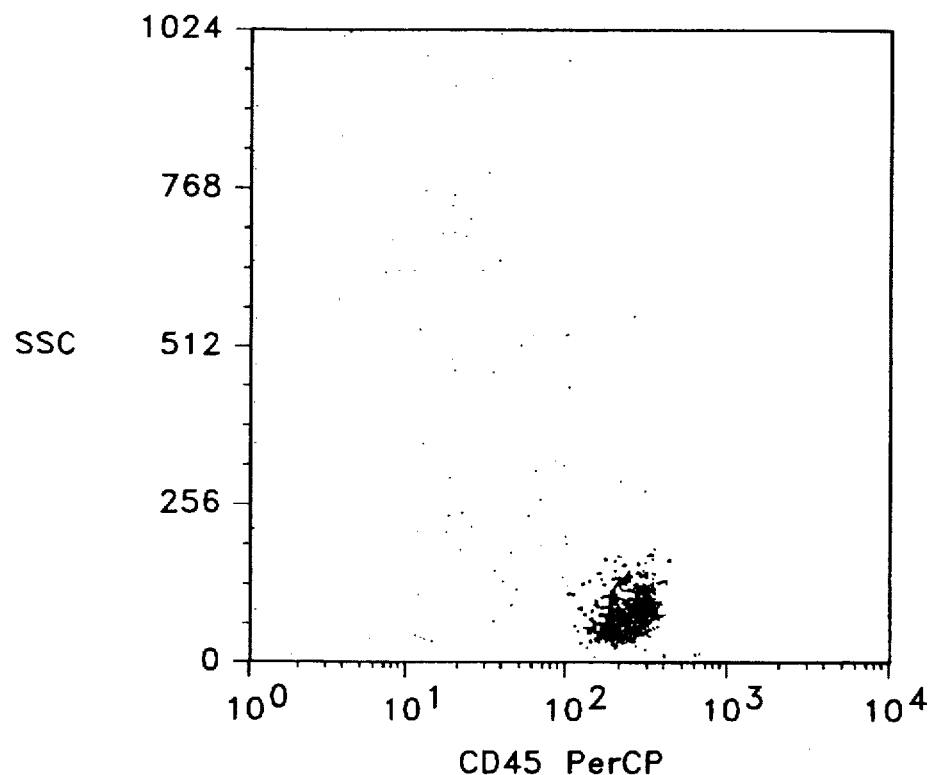
FIGS. 5A–5B illustrate a three-part differential blood count (T, B and NK cells) with CD4/CD8 T-cell subsetting using the lyse, no-wash methodology of the invention with cluster analysis performed using attractors software.
Figure 5B:
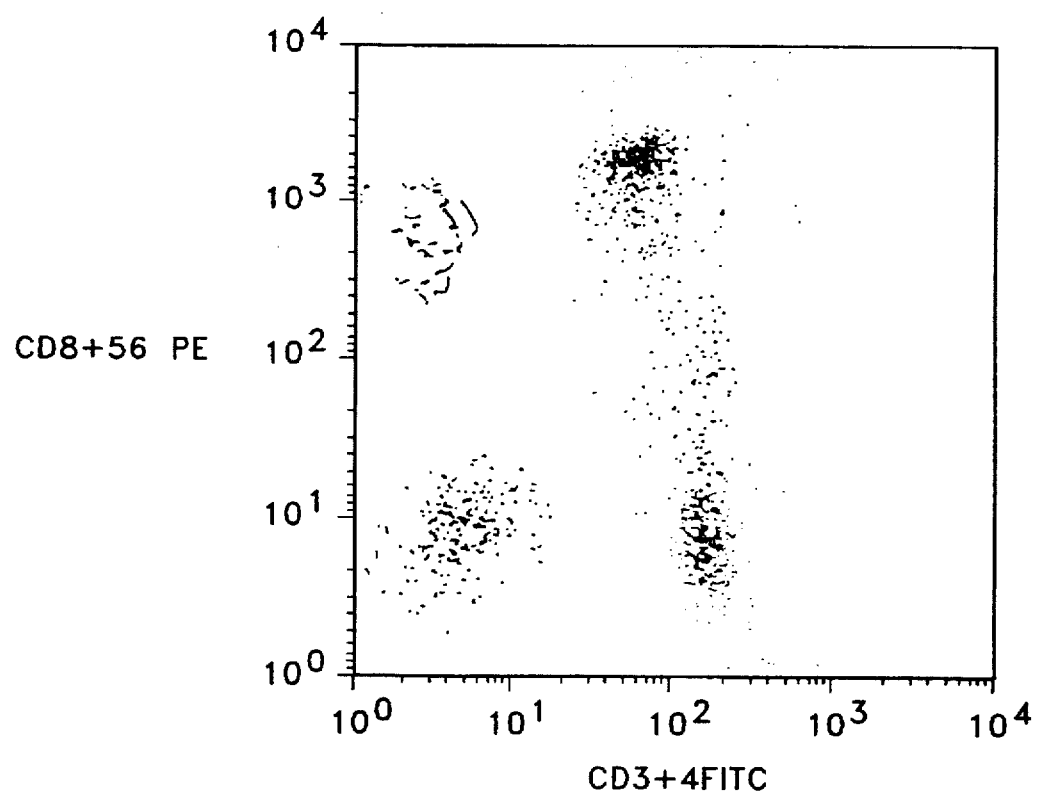

A single aliquot of blood was simultaneously stained with anti-HLE-1-PerCP, anti-Leu-3-FITC, anti-Leu-4-FITC, anti-Leu-2-PE and anti-NCAM Leu-19-PE, and lysed without washing as previously described. The stained sample was analyzed on a FACSCAN, triggering on PerCP fluorescence. FSC, SSC and fluorescence data for each event detected were acquired and analyzed using attractors software to identify the lymphocyte cluster. FIG. 5A shows the lymphocyte subpopulation free of debris and myeloid cells after analysis using "Attractors" software. To identify $T_{helper}$, $T_{supressor}$, B and NK cell subsets, dotplots of anti-Leu-3-FITC+anti-Leu-4-FITC (CD3+CD4 FITC) vs. anti-Leu-2-PE+anti-NCAM Leu-19-PE (CD8+CD56PE) were generated (FIG. 5B) and the percent of total lymphocytes in each subset calculated.

What is claimed is:

1. A method of determining a preselected lymphocyte subpopulation in a population of leukocytes in a blood sample comprising classifying the preselected lymphocyte subpopulation into one of at least two or more cell clusters by flow cytometry, comprising:

a) labeling the leukocytes in the sample with a fluorochrome-labeled primary antibody which specifically binds to a leukocyte antigen present in different amounts on each leukocyte subpopulation in said population of leukocytes whereby the labeled primary antibody binds to the preselected lymphocyte subpopulation and at least one additional leukocyte subpopulation with a different fluorescent intensity;

b) lysing erythrocytes in the sample by addition of a lysing reagent;

c) analyzing the labeled leukocytes in the lysed sample on a flow cytometer without separating the labeled leukocytes from the lysing reagent, triggering on fluorescence emission from the labeled primary antibody;

d) acquiring fluorescence intensity and light scattering data for the labeled leukocytes;

e) classifying the labeled leukocytes by establishing a geometric boundary surface based on the acquired labeled primary antibody fluorescence versus light scatter data for each of said two or more cell cluster by i) manually positioning a first geometric boundary surface on a series of two-dimensional scatterplots for at least the one cell cluster expected to contain the preselected lymphocyte subpopulation of interest, said first geometric boundary surface having a user-defined center location, shape, size, radius, and orientation;

ii) displaying the acquired fluoresence intensity and light scatter data for each cell in the scatterplots;

iii) defining a vector for each cell analyzed and testing if the vector is contained within the first geometric boundary surface;

iv) summing each vector contained within the first geometric boundary surface to calculate a vector mean;

v) after a user-defined number of vectors are summed to calculate the vector mean, calculating a new center location for the first geometric boundary surface using the calculated vector mean;

vi) moving the first geometric boundary surface on the set of said two-dimensional scatterplots to relocate the first geometric boundary surface about the new center location;

vii) repeating steps iii)–vi) until a user-defined number of vectors or all available vectors have been included in the calculation of a final center location;

viii) moving the first geometric boundary surface on the set of the two-dimensional scatterplots to relocate the first geometric boundary surface about the final center location; and, ix) classifying all subsequently received blood cells by comparing the subsequent blood cells with the first geometric boundary surface for inclusion within or exclusion outside the cluster associated with the first geometric boundary surface about the final center location; and, f) determining the presence or amount of the preselected lymphocyte subpopulation in the blood sample based upon the presence or amount of cells included within the cluster of step e) ix).

2. A method of determining a preselected lymphocyte subpopulation in a population of leukocytes in a blood sample comprising:

a) labeling the leukocytes in the sample with a fluorochrome-labeled primary antibody which specifically binds to a leukocyte antigen present in different amounts on each leukocyte subpopulation in said population of leukocytes whereby the primary antibody binds to the preselected lymphocyte subpopulation and at least one additional leukocyte subpopulation with a different fluorescent intensity;

b) analyzing the labeled leukocytes on a flow cytometer;

c) acquiring fluorescence intensity, side light scatter (SSC) and forward light scatter (FSC) data for the labeled leukocytes;

d) establishing a first lymphocyte gate based on analysis of the SSC data versus the FSC data;

e) establishing a second lymphocyte gate based on analysis of the SSC data versus the labeled primary antibody fluorescence intensity data; and, f) establishing a third lymphocyte gate by selecting the lymphocytes included in both the first and second lymphocyte gates to determine the presence or amount of the preselected lymphocyte subpopulation in the sample, wherein the first and second lymphocyte gates are each established by classifying the leukocyte population in the sample into at least two cell clusters, said classifying comprising:

i) manually positioning a gate on a series of two-dimensional scatterplots for at least the one cell cluster expected to contain the preselected lymphocyte subpopulation of interest, said gate having a user-defined center location, shape, size, radius, and orientation;

ii) displaying at least two of the three data parameters of step c) for each cell in the scatterplots;

iii) defining a vector for each cell analyzed and testing if the vector is contained within the gate;

iv) summing each vector contained within the first geometric boundary surface to calculate a vector mean;

v) after a user-defined number of vectors are summed to calculate the vector mean, calculating a new center location for the gate using the calculated vector mean;

vi) moving the gate on the set of said two-dimensional scatterplots to relocate the gate about the new center location;

vii) repeating steps iii)–vi) until a user-defined number of vectors or all available vectors have been included in the calculation of a final center location;

viii) moving the gate on the set of the two-dimensional scatterplots to relocate the gate about the final center location; and, ix) classifying all subsequently received blood cells by as being within or without the at least one cell cluster by determining whether the subsequent blood cells are included within the gate about the final center location or not.

* * * * *